(12) United States Patent
Belitsch

(10) Patent No.: US 8,413,488 B2
(45) Date of Patent: Apr. 9, 2013

(54) MEASURING PROCEDURE AND MEASURING DEVICE FOR MEASURING PHYSICAL QUANTITIES OF NON-COMPRESSIBLE MEDIA

(76) Inventor: Wolfgang Belitsch, Hart (AT)

( * ) Notice: Subject to any disclaimer, the term of this patent is extended or adjusted under 35 U.S.C. 154(b) by 218 days.

(21) Appl. No.: 12/786,134

(22) Filed: May 24, 2010

(65) Prior Publication Data

US 2011/0126614 A1 Jun. 2, 2011

(30) Foreign Application Priority Data

May 25, 2009 (AT) .................................. A 807/2009

(51) Int. Cl.
*G01N 11/08* (2006.01)
*G01N 21/00* (2006.01)
*G01N 11/00* (2006.01)
*G01N 11/06* (2006.01)

(52) U.S. Cl.
USPC ........................................ 73/54.09; 73/54.14

(58) Field of Classification Search .................. 73/54.01, 73/54.02, 54.04, 54.06, 54.09, 54.11, 54.13, 73/54.14
See application file for complete search history.

(56) References Cited

U.S. PATENT DOCUMENTS 5,331,843 A * 7/1994 Gramatte et al. ............ 73/54.09

FOREIGN PATENT DOCUMENTS

| DE | 4218284 C1 | 2/1994 |
| DE | 4315455 A1 | * 11/1994 |
| DE | 19633846 A1 | 3/1997 |
| DE | 102007025067 | * 12/2007 |
| DE | 102007025067 A1 | 12/2007 |
| GB | 1220313 | 1/1971 |

OTHER PUBLICATIONS

Lemke, Klaus, English machine translation of DE102007025067, Dec. 6, 2007; (machine translated on Apr. 24, 2012).*
Merkel, Wolfgang, English human translation of DE 4315455, Nov. 17, 1994; (human translation received Apr. 19, 2012).*

* cited by examiner

*Primary Examiner* — Peter Macchiarolo
*Assistant Examiner* — Natalie Huls
(74) *Attorney, Agent, or Firm* — Workman Nydegger

(57) ABSTRACT

A method for measuring the dynamic viscosity and the density as physical quantities of an essentially non-compressible measuring medium may include introducing a non-compressible measuring medium in a vessel charged with a compressible medium, where the non-compressible measuring medium constitutes a fraction volume of a total volume of the vessel. The method further includes measuring an initial pressure of the compressible medium, modifying the total volume of the vessel by a predetermined modification volume, and measuring a modified internal pressure of the compressible medium in the vessel effected by the volume modification. Finally, the method may include causing liquid measuring medium to flow through an opening of the vessel through a capillary tube, where the modification internal pressure is measured at one measuring point and where the initial pressure of the compressible medium surrounding the liquid measuring medium is measured after discharge out of the capillary tube.

5 Claims, 4 Drawing Sheets

MEASURING PROCEDURE AND MEASURING DEVICE FOR MEASURING PHYSICAL QUANTITIES OF NON-COMPRESSIBLE MEDIA

CROSS-REFERENCE TO RELATED APPLICATIONS

This application claims the benefit under 35 U.S.C. §119 of Austrian Patent Application No. A807/2009, filed May 25, 2009, which is incorporated herein by reference in its entirety.

BACKGROUND

The invention relates to a measuring procedure for measuring physical quantities of an essentially non-compressible medium.

BRIEF SUMMARY

The invention further relates to a measuring device for measuring physical quantities of an essentially non-compressible measuring medium, with a vessel having a total volume and being charged with a compressible medium, into which a fraction of the volume may be introduced, and with pressure measuring means for measuring an initial pressure and a modification internal pressure within the vessel. Such a measuring procedure and such a measuring device have been published in the document DE 196 33 846 A1. In the measuring procedure disclosed in this document, the volume of a solid, liquid, foam-like or porous physical body and measuring medium, respectively, is evaluated. In a first step of the process, the measuring device is calibrated. For this reason, quantities of the liquid are calibrated in a first measuring chamber combinable with atmospheric pressure and a second measuring chamber permanently combined with atmospheric pressure, respectively. After introduction of the body into a provided chamber, the calibrating quantities of liquid in the two measuring chambers are repeatedly measured in a second process step. By means of subtraction and through forming a ratio of the quantities of liquid measured and by means of multiplication by the volume of the empty chamber, the volume of the physical body may be evaluated. This measuring principle is used with so-called pycnometers.

The measuring procedure already known and the measuring device already known have proved disadvantageous insofar as the process of calibration and measurement requires numerous manual manipulations and hence is time-consuming and error-prone. In one of the process steps, for example, there occurred an error in reading the quantity of liquid contained in one of the two measuring chambers. Also the manipulation of the valve in the course of the individual process steps requires a certain amount of expert knowledge and routine.

Further, the volume of the measuring chamber has to be precisely measured in advance in order to provide for the measurement of the volume of the body. Therefore it is only possible to effect a relative measurement in regard to the volume of the measuring chamber determined in advance.

Due to the flexible connecting tubes and the valves, the exact evaluation of the volume unknown is, disadvantageously, rather limited. The measuring device known is further relatively big and may not be miniaturised. The two scales, which also include the valve, make the measuring device rather expensive, and the weight of the tubes falsifies the result of the measurement.

The documents DE 43 15 455 A1, DE 102007025067 A1 and GB 1 220 313 A each describe measuring procedures and measuring devices, respectively, provided for measuring physical quantities of an essentially non-compressible measuring medium. Therefore, the non-compressible measuring medium is measured in a vessel charged with the compressible medium. There is determined the total volume of the vessel before and after a modification of volume, with the modification of volume being realised by means of a slidable piston and the evaluation being performed on the basis of Boyle-Mariott's Law.

These known measuring procedures and measuring devices, however, have proved disadvantageous insofar as certain physical quantities of a liquid measuring medium, and here especially the dynamic viscosity and the density of the liquid measuring medium, cannot be measured.

SUMMARY OF SOME EXAMPLE EMBODIMENTS

The invention is intended to provide a measuring procedure according to the type described in the first paragraph and a measuring device according to the kind described in the second paragraph, while the disadvantages mentioned before are being prevented. In order to find a solution to the task specified above, such a measuring procedure includes the following process steps:

In a first process step, the measuring medium is introduced in a vessel charged with a compressible medium, whereas the measuring medium constitutes a fraction volume of the total volume of the vessel. In a second process step an initial pressure of the compressible measuring medium is measured. In a third process step the total volume of the vessel is modified by a given modification volume.

In a fourth process step a modification of internal pressure, effected by the modification of volume, of the compressible medium in a vessel is measured. In a fifth process step a liquid measuring medium flows through at least one opening of the vessel through a capillary tube, whereas the modification internal pressure is measured at least at one time of measurement and whereas in the second process step the initial pressure of the compressible medium, which encloses the liquid measuring medium after exiting the capillary tube, is measured.

In order to find a solution thereto, there is made provision in such a measuring device that there are provided modification means for compressing and decompressing, respectively, the compressible medium, by which the total volume of the vessel may be modified by a given modification volume, and that there are formed the pressure measuring means for measuring the modification internal pressure of the compressible medium in the vessel following the compression and decompression, respectively, of the modification means, and that there is provided a collection vessel which is connected through an opening of the vessel and a capillary tube with the vessel and which is provided for collecting a liquid measuring medium.

By the characteristics according to the invention there is accomplished that the measuring data required for the calculation of the various physical quantities of the measuring media, and here especially of the dynamic viscosity and the density, are kept very simple and may be also automatically evaluated, if necessary. The measurement may be realised by means of compression or decompression, respectively, of the compressible medium in the vessel by the modification volume. With the predetermined modification volume, which is the same in any measuring process, the measurement is reduced to a pressure measurement of the initial pressure of the modification internal pressure after the compression or decompression of the compressible medium. In this way, the measuring procedure and the measuring device are less prone to errors, this resulting in reliable and exact measurement data.

Due to the high level of sensitivity of the pressure sensors conventionally available, a very high resolution of the volume of the measuring medium introduced into the vessel is possible. Another advantage is that the measuring device according to the invention may be greatly reduced in size and hence provides for an easy transport. It is especially advantageous that the measuring device according to the invention is neither storage-nor shock-sensitive. In this way there is provided a very robust, simple and small measuring device with high resolution of measurement. Furthermore, in the measurement procedure of the invention the volume of the vessel has to be determined in advance by means of another method, in this way enabling an absolute measurement.

It is to be noted that measuring devices such as, for example, of the companies Mettler-Toledo, Kern, Imeter for measuring the volume or the solid body density of measuring media are known to those skilled in the art. In this connection, the measuring medium formed by a solid body is introduced in a measuring liquid for measurement. It is of disadvantage, however, that there is not provided a permanent and total moistening of the porous solid body. Air is frequently retained in the pores, thus reducing the measuring accuracy of well-known measuring devices. Furthermore, there is to be used an appropriate measuring liquid undergoing no chemical reaction with the solid body (for instance, in the case of samples in powder form), as this, in general, is associated with a modification of volume. In this case, it is rather elaborate or nearly impossible to recover the originally powdery sample.

In the measurement procedure according to the invention and the measuring device according to the invention there is, however, given the advantage that the measurement is performed in a contact-free form, which means that the measuring medium is not contaminated with a liquid necessary for measurement. Hence the measuring medium may be further used immediately after the measurement, without there being required a special cleaning procedure.

By converting the volume measurement of the measuring medium into a pressure measurement, it is made possible to realise a totally automatable measurement procedure. At first, after introducing the measuring medium to be measured, there is measured the initial pressure, whereafter the total volume of the vessel is reduced or increased by the modification volume, and finally the modification internal pressure in the vessel is measured. All these process steps may be controlled by means of a computer of the measuring device, hence the process may be realised virtually without being prone to errors.

There is provided a simple method of calculation on the basis of the evaluation of the measurement data measured by means of Boyle's Law. For this reason the processing power required therefore may be kept rather reduced.

By providing evaluation means formed for evaluating a mass information of the measuring medium and the volume of the measuring medium determined, the measuring device according to the invention, in addition to the evaluation of the volume of the measuring medium, may also be used for evaluating the density of the measuring medium, this being especially preferable for the use of the measuring device.

By forming the modification means as pistons in a cylinder, in order to reduce or enlarge the total volume by the modification volume, it is an especially simple and practicable embodiment of the measuring device according to the invention.

There is to be noted that a capillary viscosimeter stipulated in the document DE 42 18 284 C1 is known in which a liquid measuring medium flows through a piston from a first vessel via a capillary tube into a second vessel. A differential pressure gauge continually measures the pressure difference of the liquid measuring medium in the first and in the second vessel. This capillary viscosimeter for measuring the viscosity of the liquid measuring medium has the disadvantage that the pressure operating on the liquid measuring medium is applied directly by a piston driven by a servo-motor. As liquids essentially cannot be compressed, any imbalance in regard to the advance of the piston effected by the servo-motor or the storage of the piston rod results in a pressure modification in the first vessel and hence provides for measurement inaccuracy.

By providing an opening in the vessel, through which the measuring medium may exit the vessel through a capillary tube or may absorbed into the vessel, and by providing the piston which consistently and continually applies the modification internal pressure on the liquid measuring medium after a single compression or decompression stroke via the compressible medium (air or any other gas), there is realised an especially high measurement accuracy. Consequently, the viscosity of the liquid measuring medium or also the chronological sequence of the liquid of the measuring medium in the vessel may be evaluated in an especially exact and also in automated form, if necessary. Furthermore, vessels in any given form with cavities inaccessible for other sensors and their content may be measured.

By evaluating the measurement data measured in the evaluation means on the basis of the Hagen-Poiseuille equation for evaluating the dynamic viscosity of the liquid measuring medium, the processing power of the evaluation means required therefore may be kept rather reduced.

By measuring the chronological course of the modification internal pressure in the vessel, the liquid of the liquid measuring medium retained in the vessel and its volume, respectively, may be continually evaluated with the help of the measurement device. In this way, expensive and error-prone liquid level-measuring sensors may be omitted.

By providing temperature stabilising means (for example, in the form of Peltier elements), the temperature of the measuring medium may be kept essentially constant during the measurement process, in this way further increasing the measurement accuracy of the physical quantities evaluated.

With the measurement device according to the invention, there may be performed a calibration measurement with an empty vessel in order to exactly evaluate the volume of the empty vessel. Advantageously, the same measurement procedure may be applied also for the subsequent evaluation of the volume of the measuring medium, hence there may be performed, in a relatively easy and, if necessary, also automated form, regular calibration measurements for further improving the measurement accuracy.

The modification means, in conformance with the invention, may be formed so that a further measuring medium for applying modification internal pressure in the vessel may be introduced by the modification means. In this way, preferably the measuring medium discharged during the following measurement process may be compensated. Furthermore, a modification means (piston) for generating a modification of volume may be omitted, in this way further reducing cost and size of the measurement device, as the measuring medium has to be introduced into the vessel anyway.

It is especially preferable to provide a vessel that is expandable, as the volume of the vessel is not supposed to be much bigger than the fraction volume of the measuring medium to be measured, in order to obtain exact measurement results. Thereby, the measuring device may be adapted to the volume of the measuring medium to be measured (for example, a big solid body) to a large extent. After enlarging the vessel, there has to be performed a simple calibration measurement for evaluating the volume of the empty and enlarged vessel before the actual measurement process is performed.

Advantageously, it is also possible to perform the measurement of a measuring medium by means of different, predetermined modification volumes. This results in a linearity examination and hence calibration of the pressure sensor or also in an enlargement of the pressure area for vessels of various volume size.

By arranging a collection vessel for the liquid measuring medium underneath the vessel, the force of gravity operating on the measuring medium may be used for evaluating the kinematic viscosity. In a first measurement process, the liquid measuring medium is pressed from the vessel into the collection vessel by means of the modification internal pressure, and in a second measurement process, it is absorbed from the collection vessel into the vessel by means of a negative modification internal pressure. The effect of the force of gravity here has to be added and subtracted, once each, in this way enabling the evaluation of the density of the liquid measuring medium and thus also the kinematic viscosity (=dynamic viscosity times density).

BRIEF DESCRIPTION OF THE DRAWINGS

In the following the invention is described with the help of four exemplary embodiments displayed in the figures, to which the invention, however, is not restricted.

DETAILED DESCRIPTION

Figure 1:
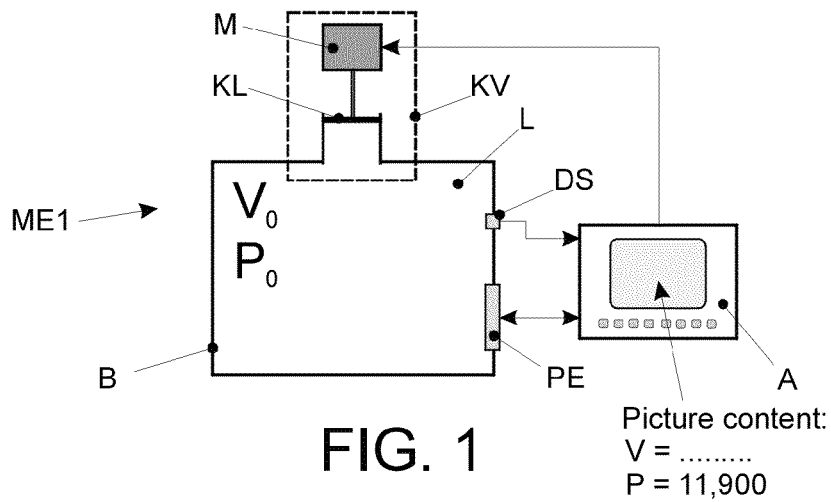
FIG. 1 shows a measuring device for measuring the volume of non-compressible bodies.

FIG. 1 shows a measuring device ME1 for measuring physical quantities of an essentially non-compressible measuring medium. Especially the volume $V_X$ of the body K may be measured with the help of the measuring device ME1. The surface of the body K here may be smooth or porous, or there may even be measured the volume $V_X$ of a powdery body K. It is especially preferable to measure the volume $V_X$ of such a body K with the measuring device ME1, if the body K does not have a geometrical form, this enabling a simple calculation of the volume $V_X$ of the body K.

The measuring device ME1 has a vessel B with a volume $V_0$, in which there is a pressure $P_0$, when the vessel is empty. In this connection, empty is determined as the body K to be measured having not been introduced into the vessel B, with the vessel B, however, already being charged with a compressible medium, this being here in this exemplary embodiment air L. A computer A forms evaluation means which are connected with the pressure sensor DS in order to measure the pressure P in the vessel B during the various process steps of the measurement procedure. The computer A further forms control means, and it is connected with a Peltier element PE via a control line, together forming temperature stabilising means for stabilising the temperature of the body K and of the air L during the performance of the measuring procedure and the measuring process, respectively.

The measuring device ME1 further comprises modification means KV provided for compressing and decompressing, respectively, the air L in the vessel B which may be used to modify the total volume $V_0$ of the vessel B by a predetermined modification volume $\Delta V$. The modification means KV comprises a servo-motor M, a cylinder and a piston KL movable in the cylinder by a servo-motor M. The computer A is connected with the servo-motor M via a control line and controls the position of the piston K in the cylinder and hence the volume of the vessel B.

Figure 2:
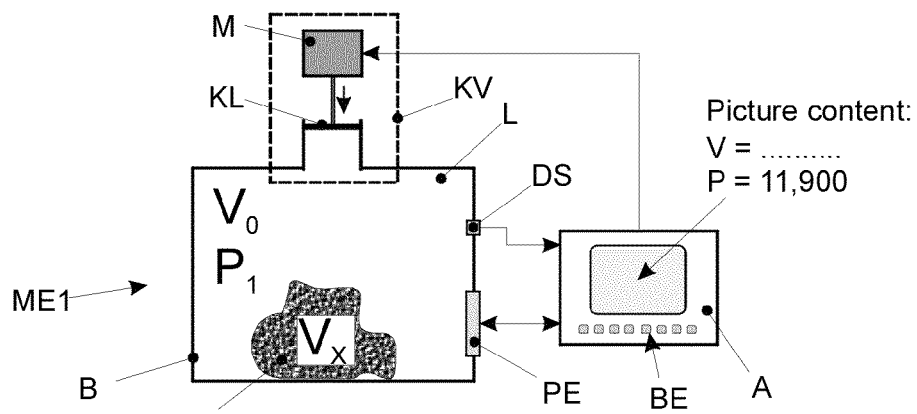
FIG. 2 shows a measuring device according to FIG. 1, after the first process step of the measuring procedure has been performed.

FIG. 2 shows a measuring device ME1 according to FIG. 1, whereas according to the first process step of the measuring procedure the body K to be measured with the volume $V_X$ to be measured was introduced into the vessel B through a gas-tight sealable opening of the vessel B (not displayed in the figures), this resulting in a pressure $P_1$ in the vessel B. As the opening of the vessel B is only gas-tight sealed after the body K has been introduced into the body K, this results in general in the pressure $P_1$ being equal to pressure $P_0$ being equal to the ambient pressure during the measurement.

Figure 3:
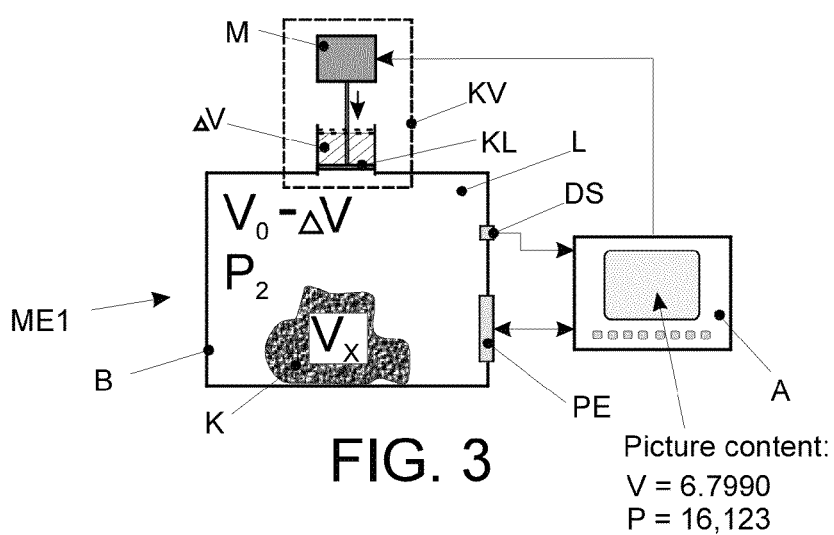
FIG. 3 shows the measuring device according to FIG. 1, after the third process step of the measuring procedure has been performed.

With the help of one of the operating elements BE of the computer A, the automated measuring procedure may be started after the body K has been introduced. According to the second process step of the measuring procedure, at this point the initial pressure $P_1$ in the vessel B is measured by the pressure sensor DS and stored in the computer A. As a consequence, the computer A gives off a control pulse to the servo-motor M in order to move the piston KL in the cylinder by a compression stroke. In this third process step of the measuring procedure the total volume $V_0$ of the vessel B is, as displayed in FIG. 3, reduced by the predetermined modification means $\Delta V$. In a fourth process step of the measuring procedure a modification internal pressure $P_2$ in the vessel B, which is effected by the volume modification ($V_0 - \Delta V$), is measured by the pressure sensor DS and stored in the computer A.

As the body K is essentially non-compressible, the air L surrounding the body K is compressed in the third process step. The more the volume $V_X$ of the body K has already filled the volume $V_0$ of the empty vessel B, the less compressible air L is surrounding the body K and the bigger is the pressure ($P_2 - P_1$) effected by the compression stroke. This dependency of the pressure difference may be evaluated in an isothermal process (temperature in the vessel B is kept constant) in accordance with $$P_2 * (V_0 - V_X - \Delta V) = P_1 * (V_0 - V_X)$$ Boyle-Mariott's-Law in order to determine the unknown volume $V_X$ of the body K, when the volume $V_0$ and the modification volume $\Delta V$ are known. For this reason, the formula is modified as follows in order to calculate, with the help of the computer A, the volume $V_X$ of the body K on the basis of the measured pressure $P_1$ and the measured modification internal pressure $P_2$.

Calculation Formula for Body and Volume: $V_X = V_0 - (1 + P1/(P2 - P1)) * \Delta V$ At the end of the automated measuring procedure, the computer A shows the volume $V_X$ of the body K on a display of the computer A. The computer A further displays the measured modification internal pressure $P_2$ in order to provide also this information to the operating personnel. The measuring device ME1 hence advantageously provides for an automated and contact-free measurement of the volume $V_X$ of the body K. In the well-known measuring procedures the body has to be introduced in a liquid measuring medium for volume measurement, this requiring a cleaning process after the measurement process has been completed. Favourably, there may be omitted such a cleaning process in this measuring device ME1 as the body K to be measured is only surrounded by air L.

Figure 4:
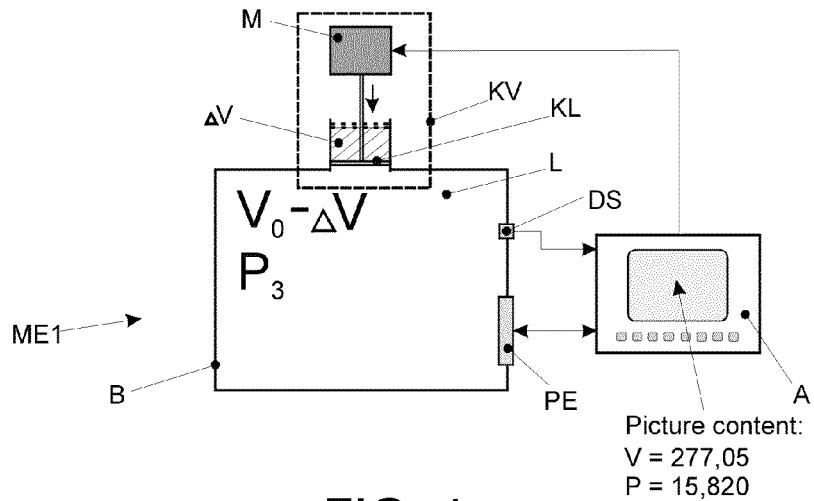
FIG. 4 shows the measuring device according to FIG. 1, while the calibration measurement is performed.

As mentioned above, the total volume $V_0$ has to be known for the calculation of the volume $V_X$. The total volume $V_0$, for example, could be taken from the data sheet of the producer of the vessel B, or it may be determined by means of another well-known method for evaluating the volume of the vessel B. For example, liquid could be filled into the vessel, and afterwards the weight of the liquid could be measured. The measuring device ME1 is favourably formed so that the total volume $V_0$ can be measured in an automated way in a calibration measurement before the first process step. As shown in FIG. 4, the compression stroke for reducing the total volume $V_0$ by the given modification volume $\Delta V$ is performed with an empty vessel B. By applying Boyle's Law, the total volume $V_0$ can be calculated by the computer A on the basis of Boyle's Law.

Calculation Formula for Vessel and Volume: $V_0 = [P_2/(P_2 - P_1)] * \Delta V$

The vessel B, for instance, could have been damaged during the transport of the measuring device ME1, resulting in a little dent, and this resulting in a modification of the total volume $V_0$ of the vessel B. By performing the calibration measurement of the actual total volume $V_0$ of the vessel B immediately before the measurement of the volume $V_X$ of the body K, there is favourably obtained an especially exact measurement result.

The measuring device ME1 is thus further formed so that the density $\rho$ of the body K can be evaluated through forming a ratio between mass information of the body K and the evaluated volume $V_X$. The measuring device ME1 has a weighing device not displayed in one of the FIGS. 1 to 4 that measures the weight of the vessel B before the body K is introduced in the vessel B and after the body K has been introduced in the vessel B. The measured weight measurement data are transmitted to the computer A which then calculates, either by subtraction of initially the weight of the body K or by processing the acceleration of gravity g=9.81 m/s$^2$, in the following the mass of the body K. After the evaluation of the volume $V_X$ by means of the above described measuring procedure, the computer A calculates the density of the body $\rho = V_X/$(mass of the body) and shows the result of this calculation on the display. The measuring device ME1 hence is favourably provided for evaluating the volume $V_X$ as well as the density $\rho$ of the body K.

It is to be noted that there might also be used another compressible medium instead of the air L. This could be, for example, a gas with especially high or especially low density. It could also be favourable in some cases of bodies to be measured to pump out air out of the vessel B before the measuring process in order to obtain nearly a vacuum in the vessel.

It is to be noted that solid bodies K, and also especially favourably powdery and liquid measuring media, may be measured with the measuring device ME1 according to the FIGS. 1 to 4. As a powder consists of tiny solid bodies, in which there are interbedded air bubbles, in the case of a compression stroke also the air in the air bubbles of the powder is compressed, and the measuring procedure evaluates the volume of the solids content of the powder. This is especially preferable if the powder is, for example, a pharmaceutical to be dissolved in the body of a patient in his body fluids, because then the volume of the solids content of the powder is important for the evaluation of the prospective effectiveness of the pharmaceutical.

It is to be noted that, instead of performing a compression stroke for compressing the compressible medium in the vessel, there may also be performed a decompression stroke for diluting and decompressing, respectively, the compressible medium. In this case there may also be applied Boyle's Law for evaluating the volume $V_X$ of the body.

It is to be noted that the air L surrounding the body K and the body K is heated by the compression stroke and cooled by the decompression stroke. These changes in temperature might result in measurement errors, as Boyle's Law is based on an isothermal process with a constant temperature course. Providing the temperature stabilising means hence increases the accuracy of the measurement data measured by the measuring device, and due to the formation of the temperature stabilising means as Peltier element PE there is obtained a cheap and practicable solution.

It is to be noted that the vessel of the measuring device may be realised in any form. For example, there may be used a balloon-like vessel, which may even be favourable, depending on the measuring medium to be measured. By means of the calibration measurement, the respective volume $V_0$ of the vessel, which may be realised in any form and gastight sealed, is evaluated before the actual measuring process. Measuring with the help of the measuring device according to the invention is even possible when the vessel shows a certain rate of leakage, through which the compressible medium might discharge during the measuring process. This leakage rate is not supposed to result in an essential change of the pressures measured during the rather short measuring process.

Figure 5:
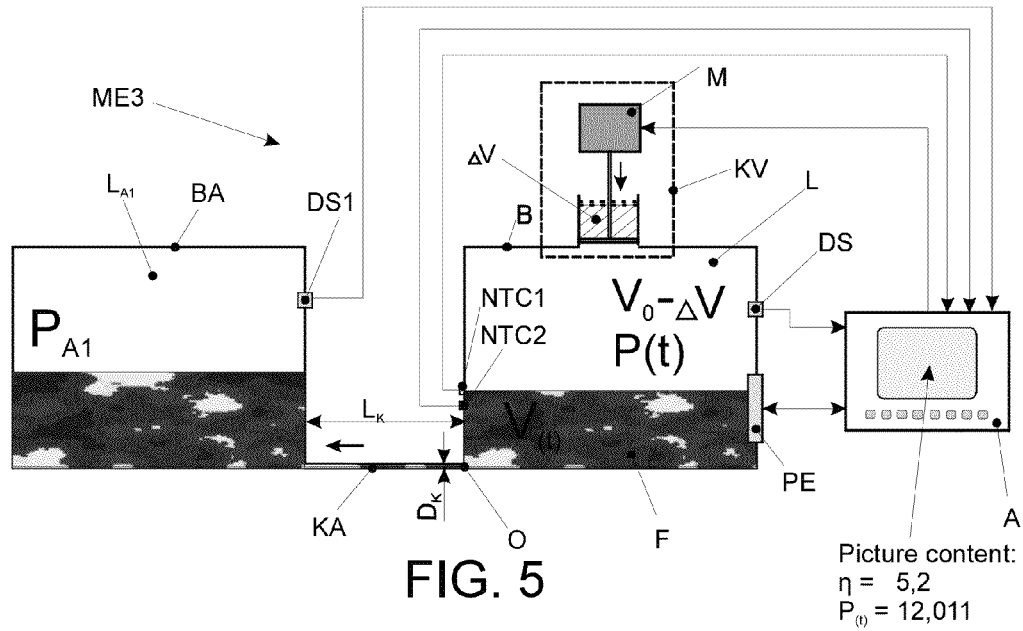
FIG. 5 shows a measuring device for measuring the dynamic viscosity of liquids according to a first exemplary embodiment of the invention, whereas a collection vessel for collecting the liquid measuring medium is formed in a closed type.

FIG. 5 shows a measuring device ME3 according to a first exemplary embodiment of the invention provided for measuring the dynamic viscosity and the density of a liquid measuring medium, the liquid F. The arrangement and operational mode of the measuring device ME3 are in accordance with the arrangement and operational mode of the measuring device ME1, with the vessel B having a capillary tube KA for docking a collection vessel BA provided for collecting the liquid F. The capillary tube KA has a very thin flow rate cross section $D_K$, through which the liquid F may only flow rather slowly through an opening O of the vessel B via the capillary tube KA into the collection vessel BA.

The viscosity of a liquid in general may be evaluated by measuring the time t required by a liquid, moved by a driving force, for streaming through a capillary tube. There is made distinction between the term "kinematic viscosity" and the term "dynamic viscosity", with the driving force for measuring the kinematic viscosity representing the dead weight of the liquid to be measured and with the driving force for measuring the dynamic viscosity being determined by a pressure difference between the pressure on the liquid at the beginning and at the end of the capillary tube. The dynamic viscosity is the actual measurement for the viscosity of the liquid. The time $\Delta t$ a certain liquid volume $\Delta V_F$ requires for streaming through the capillary tube KA with the length $L_K$ and the diameter $D_K$ (=2*R) as a consequence of the pressure difference $\Delta P$ is related with the dynamic viscosity of the liquid F as follows:

Hagen-Poiseuille Equation: $\Delta V_F/\Delta t = \pi R^4 * \Delta P/(8*L_K*\eta)$ A further pressure sensor DS1 is provided in the collection vessel BA in order to measure the initial pressure $P_{A1}$ in the air $L_{A1}$ surrounding the liquid F after exiting the capillary tube KA in the collection vessel BA in the second process step. The vessel B now has further liquid level measuring means formed by a first NTC resistance NTC1 and a second NTC resistance NTC2 as well as evaluation means provided in the computer A. The NTC resistances are heated electrically, and they are then cooled by the liquid F streaming along the inner side of the vessel F, whereas the NTC resistances are cooled differently, dependent on whether liquid F or air L streams along the inner side of the vessel B. In this way, the computer A is enabled to measure the discharging of a certain liquid amount $\Delta V_F$ out of the vessel B into the collection vessel BA.

The operating mode of the measuring device ME3 according to the first exemplary embodiment is in the following described with the help of the measuring procedure performed by the measuring device ME3. In the first process step the liquid F is introduced into an opening of the vessel B also not displayed in FIG. 5. In this first process step there is opened an opening (also not displayed in FIG. 5) of the collection vessel BA positioned in the topside of the collection vessel BA, thus enabling the discharge of air $L_{A1}$ out of the collection vessel BA. The liquid F flows via the capillary tube KA from the vessel B into the collection vessel BA until there is obtained in both vessels B and BA a liquid level of the same height according to the law of communicating vessels. This is necessary so that in the subsequent measurement process the pressure difference in the two vessels B and BA forms the driving force for measuring the dynamic viscosity. Then the two openings in the vessels B and BA are sealed airtight, and the automated measurement process is started by manipulation of the control element of the computer A.

In the second process step the further pressure sensor DS1 measures the initial pressure $P_{A1}$ in the collection vessel AB, and the data is stored in the computer A. In the third process step, the modification means KV already described comprehensively with the help of the measuring device ME1 perform the compression stroke, in which the air F surrounding the liquid F in the vessel B is compressed and in which the modification internal pressure P(t) is set in the air L, which is then measured in the fourth process step by the pressure sensor DS. The pressure difference $\Delta P=P(t)-P_{A1}$ now forms the driving force, by means of which the liquid F flows from the vessel B via the capillary tube KA into the collection vessel BA.

The computer A then measures the time $\Delta t$ required by the liquid amount $\Delta V_F$, determined by the distance of the two NTC resistances NTC1 and NTC2, for discharging. Subsequently, the computer A calculates, by using the Hagen-Poiseuille equation, the dynamic viscosity of the liquid F as follows:

Dynamic Viscosity $\eta=(\Delta t*\Delta P*\pi*R^4)/(8*L_K*\Delta V_F)$

It is to be noted that the liquid level measuring means may also be formed by optical measuring means well known to persons skilled in this art.

It is to be noted that the modification internal pressure P(t) decreases with proceeding measurement time t, as the liquid discharging from the vessel B reduces the modification internal pressure P(t) in the vessel B and the liquid flowing into the collection vessel BA increases the initial pressure $P_{A1}$. As only a small amount of liquid $\Delta V_F$ flows through the capillary tube KA, this effect of modifying the pressures P(t) and $P_{A1}$ in the vessels B and BA may be omitted. In order to increase measurement accuracy, it may be preferable to simultaneously measure the modification internal pressure P(t) as well as the initial pressure at several measurement points t and then to take the data into account in the calculation formula for calculating the dynamic viscosity.

It is to be noted that the liquid level measuring means may be totally omitted, and that there may be drawn a conclusion from the measurement of the change in pressure difference $\Delta P=P(t)-P_{A1}$ to the liquid flown from the vessel B into the collection vessel BA. Favourably, the measurement of the liquid level of a liquid in a vessel may be based on a pressure measurement. Based on the principle according to the invention, there is possible a multiplicity of applications for a person skilled in this field.

A further and more essential advantage of measuring the chronologically variable liquid level over the chronologically modified pressure P(t) is that we do not have to wait until the entire liquid between NTC1 and NTC2 is discharged, which might result in variably long measurement lengths. Hence the measurement of a liquid with a dynamic viscosity of 1000 mPas would take about 1,000 times longer than the measurement of a liquid with 1 mPas.

By means of the "pressure procedure", the liquid discharged may be measured through the pressure modification during a determined period of time (for example, 10 s, 20 s), which would then result in equal measuring times for a liquid with 1000 mPas as well as for a liquid with 1 mPas. Therewith, the measurement range of viscosity of a capillary tube with a set internal diameter $D_K$ is essentially increased. Furthermore, a variable (but nevertheless exactly defined) $\Delta V$ can increase the initial pressure for liquids with higher viscosity in order to obtain a greater pressure modification during the period of measurement.

It is to be noted that introducing the liquid F may also be controlled by the computer A in an automated way through the injection cylinders, as the computer A may control the opening as well as closing of the openings of the vessels B and BA. In this way there would favourably be obtained a completely automated measurement procedure according to the invention.

It is to be noted that the measurement process may also be performed if the collection vessel BA has not been vented before the measurement in order to establish a uniform liquid level in both vessels. In this case, the initial pressure $P_{A1}$ would be higher than the ambient pressure, which may, however, be disregarded as there will only be taken into account the differential pressure before and after the capillary tube KA.

Figure 6:
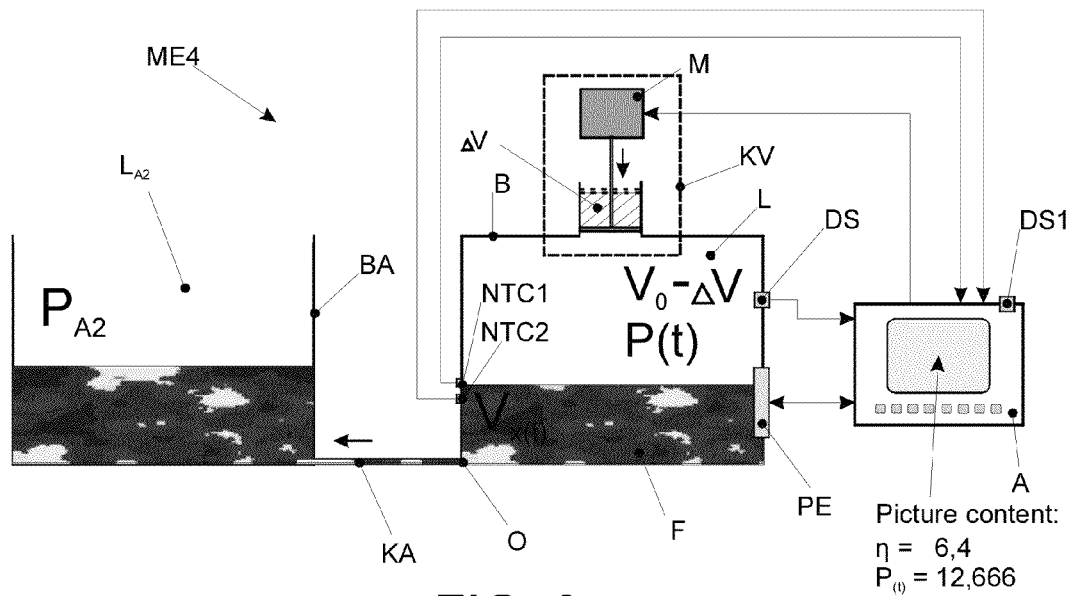
FIG. 6 shows a measuring device for measuring the dynamic viscosity of liquids according to a second exemplary embodiment of the invention, whereas a collection vessel is formed in an open type.

FIG. 6 shows a measuring device ME4 according to a second exemplary embodiment of the invention. The arrangement and the operating mode of the measuring device ME4 are in this case identical with the arrangement and the operating mode of the measuring device ME3 according to FIG. 5, with the collection vessel BA being formed open towards the top; this is why the ambient pressure of the air $L_{A2}$ as initial pressure $P_{A2}$ always operates on the liquid F after discharge out of the capillary tube KA. The other pressure sensor DS1 for measuring the initial pressure $P_{A2}$ is hence measured at the measuring device ME4 immediately at the computer A. This open construction of the collection vessel BA simplifies the measuring procedure, as the collection vessel BA needs not be equipped with a gastight sealable opening that has to be opened and closed at predetermined points of time. Furthermore, a measurement of the initial pressure $P_{A2}$ at various points of time may be omitted, as the ambient pressure—at least during the very restricted duration of the measurement—stays constant.

Figure 7:
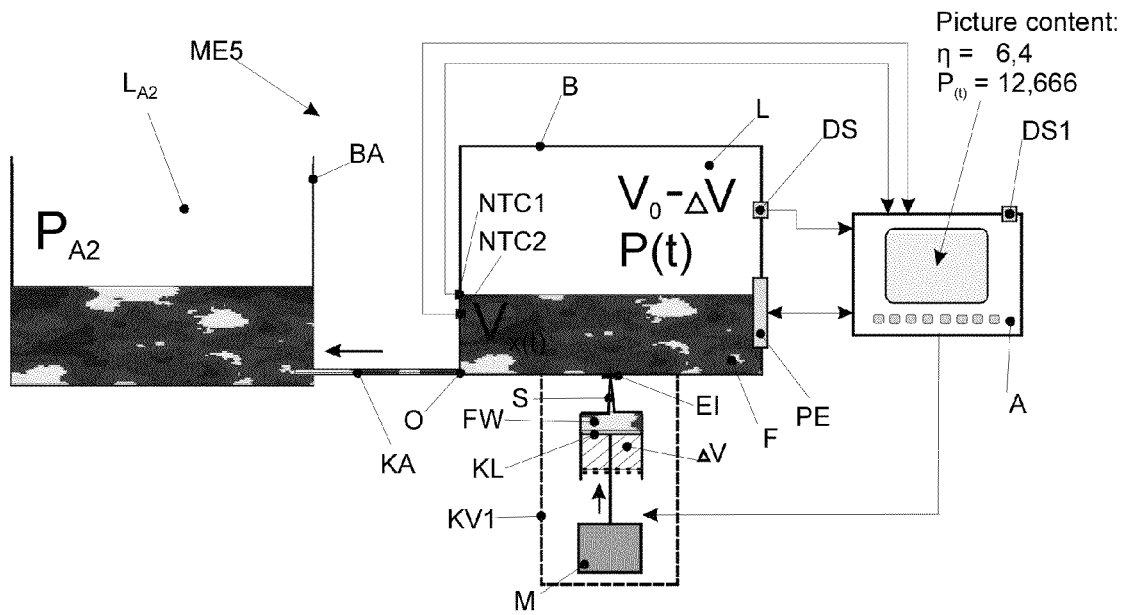
FIG. 7 shows a measuring device for measuring the dynamic viscosity of liquids according to a third exemplary embodiment of the invention, in which there is injected a further measuring medium in the vessel in the third process step.

FIG. 7 shows a measuring device ME5 according to a third exemplary embodiment of the invention. The arrangement and the operating mode of the measuring device ME5 are in this case essentially the same as the arrangement and the operating mode of the measuring device ME4 according to FIG. 6, with the modification means KV1 being formed so that in the third process step further liquid FW is introduced into the vessel B, thereby modifying the total volume $V_0$ of the vessel B by the predetermined modification volume $\Delta V$.

The modification means KV1 for this reason are provided with a nozzle S at the cylinder, injecting the further liquid FW contained in the cylinder through a sealing gasket EI in the bottom of the vessel B into the vessel B in the third process step. In this way, the fraction volume $V_{X(t)}$ is increased by the modification volume $\Delta V$, resulting in an appropriate decrease of the volume remaining for the air, this resulting in a compression of the air L and hence in an increase of the pressure. Apart from the third process step, the evaluation of the dynamic viscosity is the same in the measuring device ME5 as in the measuring device ME4 according to FIG. 6. In this third exemplary embodiment, there is presented the advantage that the measuring medium discharging during the subsequent measurement process is compensated and that there is not necessary any additional means for creating the pressure over $\Delta V$.

Figure 8:
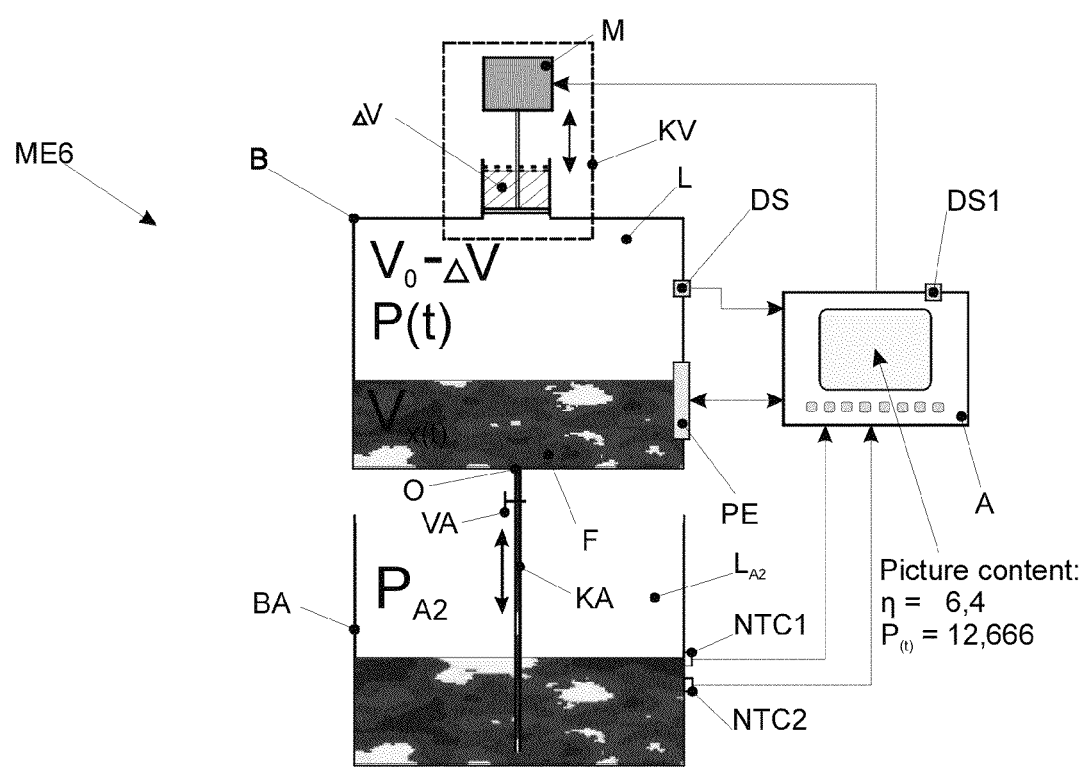
FIG. 8 shows a measuring device for measuring the dynamic viscosity of liquids according to a fourth exemplary embodiment of the invention, in which the collection vessel is arranged under the vessel containing the liquid measuring medium to be measured.

FIG. 8 shows a measuring device ME6 according to a fourth exemplary embodiment of the invention. The arrangement and the operating mode of the vessel B and of the modification means KV of the measuring device ME6 here are essentially the same as the arrangement and the operating mode of the measuring device ME4 according to FIG. 6, with the collection vessel BA being arranged beneath the vessel B in the measuring device ME6. As a driving force in order to drive the liquid F from the vessel B into the collection vessel BA, there is used force of gravity as well as the pressure difference between the pressures in the vessels B and BA. A lock valve VA prevents an immediate discharge of the liquid F before the measurement process is started.

In the measuring device ME6 there are then performed two measurement processes, with a compression stroke being performed with the modification means KV in the first measurement process, which then results in the force of gravity as well as the pressure difference pressing the liquid F from the vessel B into the collection vessel BA. The time $\Delta t$ required by the predetermined liquid amount $\Delta V_F$ for discharging into the collection vessel Ba is measured by the computer A. Subsequently, there is performed a decompression stroke in the second measurement process, with the force of gravity, however, still operating on the liquid F, but here the suction force, which is essentially stronger, results in a reflux of the liquid F from the collection vessel BA into the vessel B, effected by the negative pressure in the vessel B. The dynamic viscosity as well as the density of the liquid may be exactly evaluated by means of the evaluations of the measurement results.

It is to be noted that the lock valve VA may also be formed in an electrically controllable valve which is controlled by the computer A after the measurement of the initial pressure $P_{AZ}$ in the second process step in order to enable the discharge of the liquid F through the capillary tube KA. Thereby, favourably a completely automated measuring procedure is obtained in the measuring device ME6 according to the fourth exemplary embodiment of the invention.

It is to be noted that the volume $V_0$ should be selected not too big in regard to volume $V_X$ so that also in the case of small volume streams (tenacious liquid) there will be measurable a significant pressure modification in a short period of time.

It is to be noted that "essentially non-compressible" means that the measuring medium in comparison with the compressible medium cannot be or can only be relatively little or negligibly little compressed. The modification means compress or decompress, by means of the volume modification, hence only or virtually only the compressible medium, and the volume modification of a, as the case may be, easily compressible measuring medium (for example, rubber) does not, or only insignificantly, effect the measurement result.

It is to be noted that the compressibility of, for example, rubber may be measured by measuring through $\Delta V$ the volume of the measuring medium rubber with negligibly little positive pressure and subsequently performing the well-known volume measurement with pressures of 1, 2, 3, ... bar as a result of the variation of $\Delta V$.

The invention claimed is:

1. A method for measuring the dynamic viscosity and the density as physical quantities of an essentially non-compressible measuring medium, the method comprising:
    introducing a non-compressible measuring medium in a vessel charged with a compressible medium, wherein the non-compressible measuring medium constitutes a fraction volume of a total volume of the vessel;
    measuring an initial pressure of the compressible medium;
    modifying the total volume of the vessel by a predetermined modification volume;
    measuring a modification internal pressure of the compressible medium in the vessel effected by the volume modification; and
    causing a liquid measuring medium to flow through at least one opening of the vessel through a capillary tube, wherein the modification internal pressure is measured at least at one measuring point and wherein the initial pressure of the compressible medium surrounding the liquid measuring medium is measured after discharge out of the capillary tube.

2. The method according to claim 1, wherein the total volume of the vessel is increased and decreased, respectively, by the modification volume, with a piston performing in a cylinder, which forms a part of the vessel, a decompression stroke and a compression stroke, respectively.

3. The method according to claim 1, wherein the measurement of the dynamic viscosity of the liquid measuring medium is obtained by evaluating the measurement data measured with the help of the Hagen-Poiseuille equation.

4. The method according to claim 1, wherein the volume of the liquid measuring medium remaining in the vessel is determined by means of an evaluation of the measuring data.

5. The method according to claim 1, further comprising:
    measuring the initial pressure and the modification internal pressure of an empty vessel and evaluating the total volume of the vessel according to Boyle-Mariotte's Law.

* * * * *